United States Patent [19]
Ueno et al.

[11] Patent Number: 6,084,101
[45] Date of Patent: Jul. 4, 2000

[54] NAPHTOL DERIVATIVE AND PROCESS FOR PRODUCING THE SAME

[75] Inventors: Ryuzo Ueno, Nishinomiya; Masaya Kitayama, Takarazuka; Kenji Minami, Sennan; Hiroyuki Wakamori, Hyogo, all of Japan

[73] Assignee: Kabushiki Kaisha Ueno Seiyaku Oyo Kenkyujo, Osaka, Japan

[21] Appl. No.: 09/077,921

[22] PCT Filed: Oct. 9, 1997

[86] PCT No.: PCT/JP97/03639

§ 371 Date: Jun. 5, 1998

§ 102(e) Date: Jun. 5, 1998

[87] PCT Pub. No.: WO98/16513

PCT Pub. Date: Apr. 23, 1998

[30] Foreign Application Priority Data

Nov. 10, 1996 [JP] Japan ..................................... 8-269985

[51] Int. Cl.$^7$ ........................ C07D 213/75; C07D 275/03
[52] U.S. Cl. ........................... 546/309; 548/161; 548/190
[58] Field of Search ............................. 546/309; 548/161, 548/190

[56] References Cited

FOREIGN PATENT DOCUMENTS

| 47-1730 | 1/1972 | Japan . |
| 61-55650 | 3/1986 | Japan . |
| WO 96/32366 | 10/1996 | WIPO . |

*Primary Examiner*—Zinna Northington Davis
*Attorney, Agent, or Firm*—Sughrue, Mion, Zinn, Macpeak & Seas, PLLC

[57] ABSTRACT

The present invention relates to a novel 2-hydroxy-naphthalene-3,6-dicarboxylic acid derivative. The compound is useful as a raw material for dyes, pigments, photosensitive materials and the like.

3 Claims, 6 Drawing Sheets

NAPHTOL DERIVATIVE AND PROCESS FOR PRODUCING THE SAME

This application is filed under 35 U.S.C. § 371 as a National Stage Application of PCT/JP97/03639 filed Oct. 9, 1997.

TECHNICAL FIELD

The present invention relates to a novel naphthol derivative which can be used as a raw material for synthesis, such as dyes, pigments, photosensitive materials and the like, and a process for producing the same.

BACKGROUND OF THE INVENTION

The naphthol derivatives is the most economical compounds among the condensed aromatic compounds which forms conjugated polyene systems and has adsorption in the electron band, and is easily used as raw materials for synthesis. Therefore, it has hitherto been used as various characteristic compounds, particularly raw materials such as dyes, pigments, photosensitive materials and the like.

As these naphthol derivatives, there have been known 2-hydroxy-3-phenylaminocarbonylnaphthalene, 2-hydroxy-6-phenylaminocarbonylnaphthalene wherein a substituent is introduced at the 3- or 6-position of 2-hydroxynaphthalene, and those wherein an alkyl or alkoxy group is added to these phenyl groups.

However, only 2-hydroxy-3,6-dihydroxycarbonyl naphthalene has been known as the naphthalene derivatives having substituents at both the 3- and 6-position of 2-hydroxynaphthalene.

An object of the present invention is to provide a novel 3,6-di-substituted-2-hydroxynaphthalene derivative, particularly 2-hydroxy-3,6-dihydroxycarbonylnaphthalene derivative, which is useful as a raw material for synthesis, and a process for producing the same.

DISCLOSURE OF THE INVENTION

The present invention relates to a naphthol derivative represented by the general formula (I):

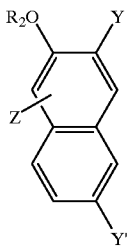

(I)

[wherein Y is —(CONH)$_n$—X or —COR,

Y' is —(CONH)$_n$—X' or —COR',

X and X' may be the same or different and represent a pyridyl group, a thiazolyl group, a benzothiazolyl group or a imidazolyl group, and each group may be optionally substituted, R and R' may be the same or different and represent a hydroxyl group, an optionally branched alkoxy group having 1 to 6 carbon atoms, a halogen atom, a benzyloxy group, a phenyloxy group or a phenacyloxy group, R$_2$ is a hydrogen atom, an alkali metal, an optionally branched alkyl group having 1 to 6 carbon atoms, an acyl group having 1 to 6 carbon atoms or a phenylalkylene group, Z is one or more sorts of groups selected from the group consisting of a hydrogen atom, a halogen atom, a nitro group, a nitroso group or an amino group (Z may be substituted on any ring of the naphthalene ring), and n is an integer of 1 or 2, provided that Y and Y' are not simultaneously —COR and —COR' respectively], and a process for producing the same.

In particular, the present invention relates to a naphthol derivative represented by the general formula (IV) or (IV'):

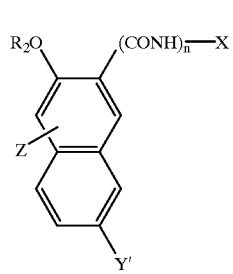

(IV)

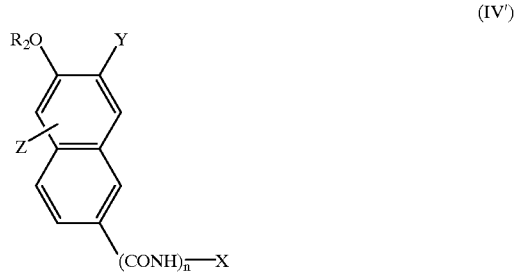

(IV')

wherein one of the substituents Y and Y' in the general formula (I) is —(CONH)$_n$—X and the other is —(CONH)$_n$—X or —COR [wherein X, n and R are as defined above].

The naphthol derivative (I) according to the present invention is a novel compound of the naphthol derivative.

The naphthol derivatives (IV) and (IV') according to the present invention are the novel compounds and are compounds wherein an optionally substituted a pyridyl, thiazolyl, benzothiazolyl or imidazolyl group is added at the 3-position and/or 6-position of 2-hydroxynaphthalene through an aminocarbonyl group or —CONHCONH— group. These residues, which are added through the aminocarbonyl or —CONHCONH— group, may be same or different at the 3-position and 6-position. The linking groups (aminocarbonyl group and —CONHCONH— group) may be also the same or different at the 3-position and 6-position.

One of the 3-position and 6-position of the naphthol derivative according to the present invention may be a hydroxycarbonyl group, an optionally branched alkoxycarbonyl group having 1 to 6 carbon atoms, a benzyloxycarbonyl group, a phenyloxycarbonyl group or a phenacyloxycarbbnyl group. The hydrogen atom of the hydroxyl group at the 2-position may be substituted by an alkali metal atom, an optionally branched alkyl group having 1 to 6 carbon atoms, an acyl group having 1 to 6 carbon atoms or a phenyl-substituted alkylene group. One or more sorts selected from the group consisting of a halogen atom, a nitro group, a nitroso group and an amino group may be introduced into the naphthalene ring.

When X is substituted a pyridyl, thiazolyl, benzothiazolyl or imidazolyl group, the following groups are exemplified as a substituent: alkyl group, alkoxy group, alkyl halide group, phenoxy group, alkoxycarbonyl group, nitro group, halogen atom, hydroxyl group, amino group, benzoylamino group, dialkylaminosulfonyl group and cyano group. As the alkyl group, an optionally branched saturated or unsaturated alkyl group having 1 to 6 carbon atoms can be used. Preferred alkyl groups include a methyl, ethyl, propyl, isopropyl, butyl or t-butyl group. As the alkoxy group, an optionally branched saturated or unsaturated alkoxy group having 1 to 6 carbon atoms can be used. Preferred alkoxy groups include a methoxy and ethoxy group. A fluorine, chlorine, bromine and iodine are exemplified as the halogen atom. The numbers of the substituents are 1 to 5, and the substituents may be the same or different.

The above naphthol derivative (IV) or (IV') according to the present invention can be produced by condensing a naphthol derivative represented by the general formula (II):

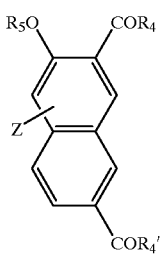
(II)

[wherein $R_4$ is a hydroxyl group or a halogen atom, $R_4'$ is a hydroxyl group, a halogen atom or an optionally branched alkoxy group having 1 to 6 carbon aotms. $R_5$ is a hydrogen atom or a protective group of a hydroxyl group, and Z is as defined above], with an heterocyclic compound represented by the general formula (III):

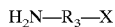
(III)

[wherein $R_3$ is a single bond or —CONH—, provided that X is as defined above].

In the formula (II), $R_5$ is a hydrogen atom, an alkali metal atom or a protective group of the hydroxyl group. The protective group of the hydroxyl group means a group capable of temporarily bonding to a hydroxyl group in order to protect said hydroxyl group during the reaction for introducing a substituent into the other positions and easily regenerating the hydroxyl group through, for example, alkali or acid hydrolysis and the like after the completion of the desirable reaction. The following groups are exemplified as the protective group: optionally branched alkyl group having 1 to 6 carbon atoms, benzyl group, acetyl group, acetonyl group, tetrahydropyranyl group, trimethylsilyl group and the like.

A phenylurea derivative, wherein $R_3$ in the compound of the formula (III) is —CONH—, can be obtained by forming an ureido group using a cyanate method of reacting the corresponding heterocyclic compounds with cyanic acid.

More specifically, as shown in the following reaction scheme (VI):

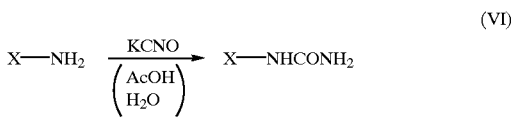
(VI)

[wherein X is as defined above], the objective compound can be obtained, for example, by dissolving a heterocyclic compound in an aqueous solution of acetic acid, adding dropwise an aqueous solution of potassium cyanate at 15° C. over 30 minutes, heating to 30° C. after completion of the addition, reacting the mixture for 30 minutes, filtering the precipitated crystal, and washing with water.

The reaction of the compounds (II) and (III) can be carried out by, for example, dissolving 2-hydroxy-3,6-dihydroxycarbonylnaphthalene and a heterocyclic compound in xylene, adding dropwise phosphorous trichloride to the solution at 90 to 100° C. and then heating the resultant solution to 140° C. and reacting for 3 hours. After completion of the reaction, water is added to the reaction mixture, said mixture is neutralized, the precipitated crystal is filtered, and the crystal on a filter paper is washed with an organic solvent such as xylene to obtain the compound (IV) or (IV').

In order to introduce a substituent other than the hydrogen atom into $R_2$, for example, the corresponding 3,6-derivative of 2-hydroxy-3,6-dihydroxycarbonylnaphthalene wherein 3-position and 6-position are protected may be reacted with a halide having the substituent to be introduced such as benzyl chloride, ethyl iodide and the like in the presence of a suitable basic substance such as potassium carbonate.

In order to introduce, for example, a halogen atom into the naphthalene ring as the substituent Z, a halogen molecule such as bromine dissolved in chloroform and the like may be added to a solution of the compound wherein the corresponding position of the naphthalene ring is unsubstituted. In order to introduce a nitroso group, an aqueous solution of sodium nitrite may be added to a solution of the compound wherein the desired position of the naphthalene ring is unsubstituted.

EXAMPLE

Example 1

Synthesis of 2-hydroxy-3,6-bis(2'-pyridylamino carbonyl)naphthalene (V)

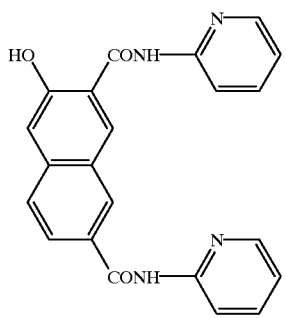

Figure 1:
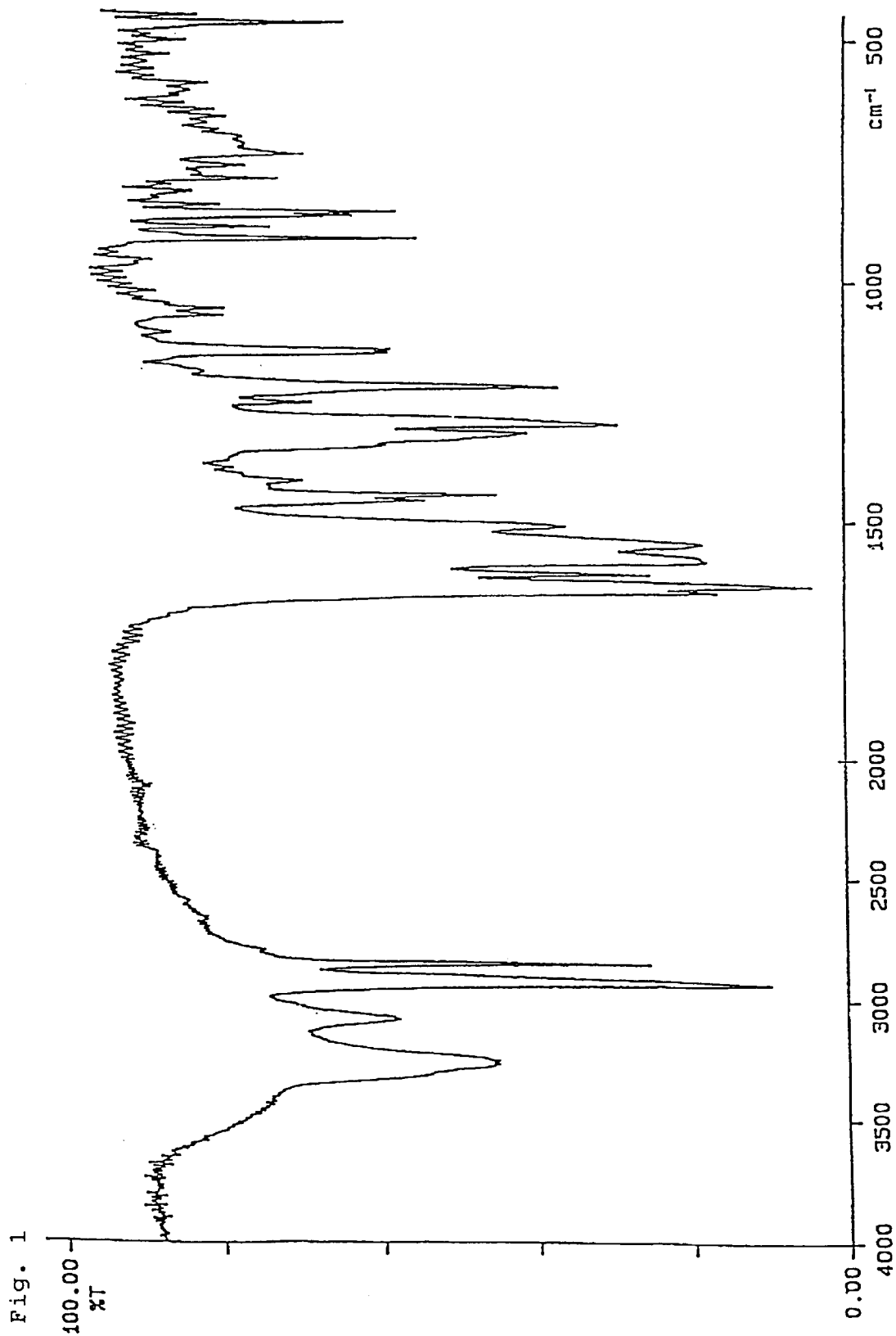
FIG. 1 is an infrared absorption spectrum of the compound obtained in Example 1.

2-Hydroxy-3,6-dihydroxycarbonylnaphthalene (14.3 g) and 2-aminopyridine (13.6 g) were dissolved in the mixture of N-methyl-2-pyrrolidone (120 g) and ethyl acetate (150 g). To this solution, dicyclohexylcarbodiimide (30.9 g) was added and the mixture was reacted at room temperature for about 15 hours. After insoluble materials were filtered off, the filtrate was concentrated to about half of its original weight and diglyme (30.6 g) was added, and the resultant mixture was heated to 170° C. After 2 hours, the reaction mixture was cooled to room temperature, and insoluble materials were filtered off. After concentration of the filtrate, ethyl acetate (200 g) was added to the concentrate, and the resultant mixture was subjected to an ultrasonic treatment to precipitate the product as a crystal which was then filtered and dried. 2-hydroxy-3,6-bis(2'-pyridylamino carbonyl) naphthalene (15.7 g) was obtained as a yellowish white powder (melting point: 311.2° C.).

An infrared absorption spectrum (KBr method) is shown in FIG. 1.

Example 2

Synthesis of 2-hydroxy-3,6-bis(thiazol-2'-ylaminocarbonyl)naphthalene (VI)

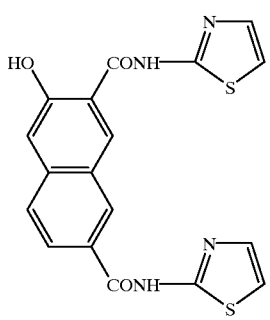

2-Aminothiazole (6.3 g) was dissolved in the mixture of N-methyl-2-pyrrolidone (50.0 g) and toluene (30.0 g) and the solution was heated to 60° C. To this solution, a solution prepared by dissolving 2-hydroxy-3,6-bischlorocarbonylnaphthalene (5.6 g) in N-methyl-2-pyrrolidone (120.0 g) was added and the mixture was heated to 80° C. After about 24 hours, the reaction mixture was concentrated, and water (470 g) was added to the concentrate. The precipitated crystal was filtered off, washed with methanol, and dried to obtain 2-hydroxy-3,6-bis (thiazol-2'-ylcarbonyl)naphthalene (1.7 g) as a skin colored powder (melting point:286.6° C.).

Figure 2:
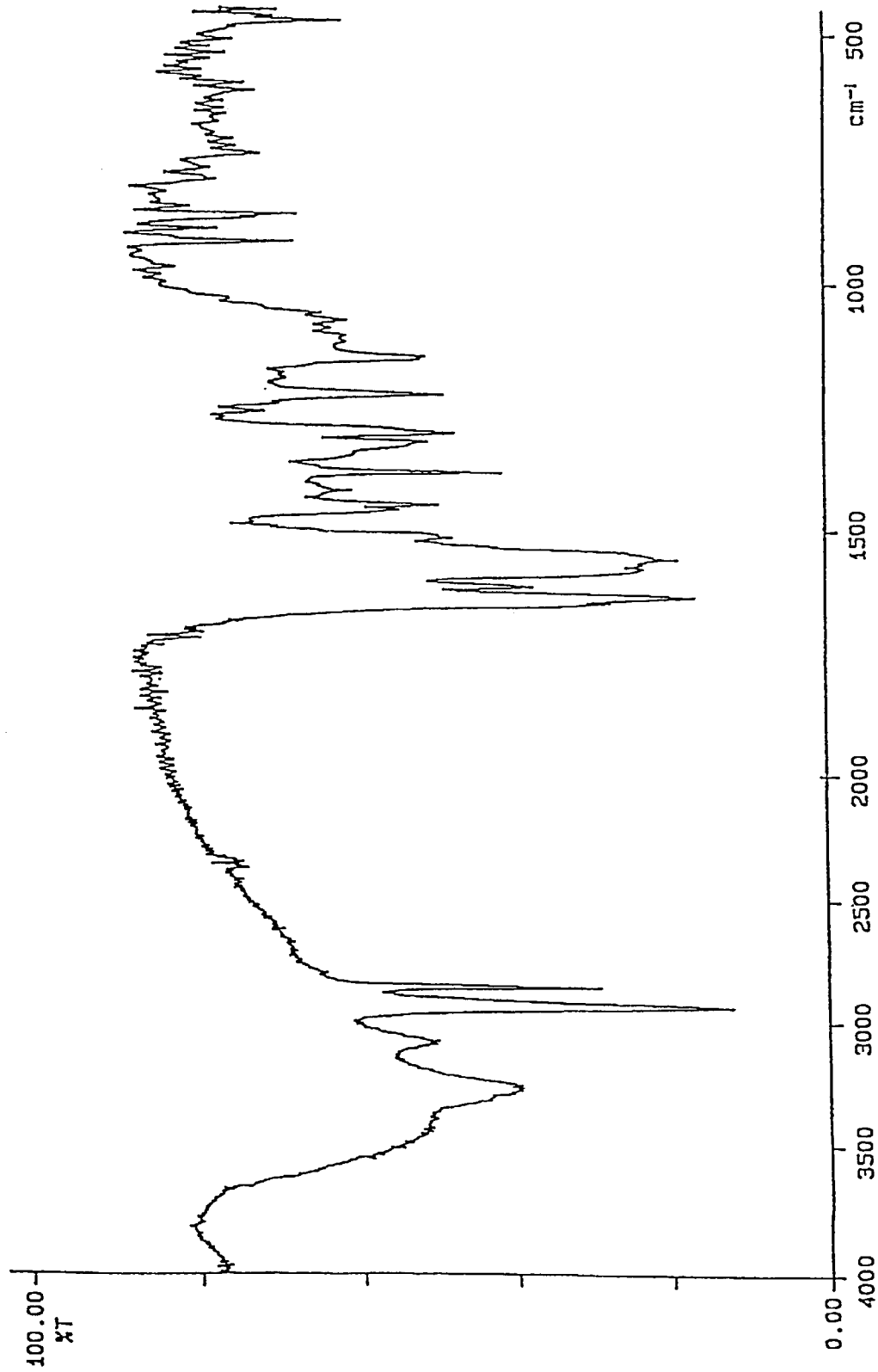
FIG. 2 is an infrared absorption spectrum of the compound obtained in Example 2.

An infrared absorption spectrum (KBr method) is shown in FIG. 2.

Example 3

Synthesis of 2-hydroxy-3,6-bis(benzothiazol-2'-ylaminocarbonyl)naphthalene (VII)

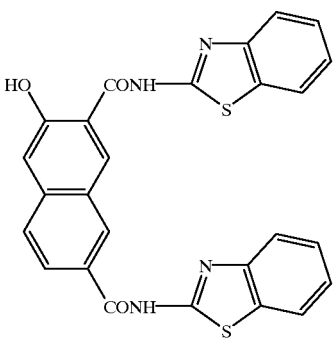

2-Hydroxy-3,6-bis(benzothiazol-2'-ylaminocarbonyl) naphthalene (3.2 g) was obtained as a skin colored powder (melting point: 364.1° C.) by the same procedure as that described in Example 2 with the exception of using 2-aminobenzothiazole (9.4 g) instead of 2-aminothiazole.

Figure 3:
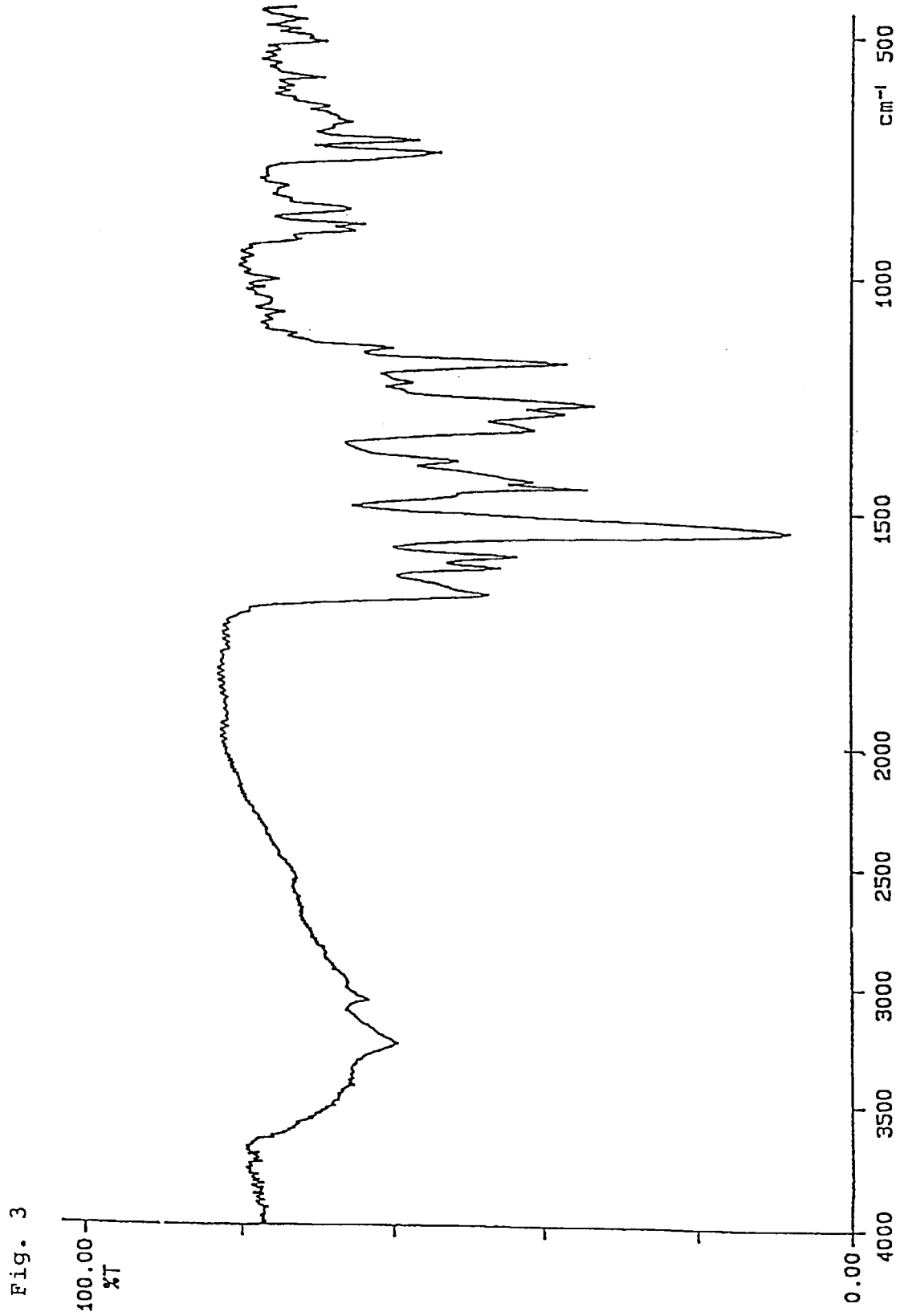
FIG. 3 is an infrared absorption spectrum of the compound obtained in Example 3.

An infrared absorption spectrum (KBr method) is shown in FIG. 3.

Example 4

Synthesis of 2-hydroxy-3,6-di(4',5'-dicyanoimidazol-2'-ylaminocarbonyl)naphthalene.

(VIII)

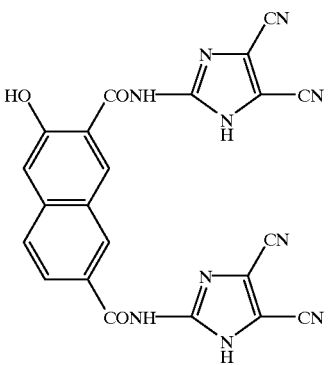

2-Hydroxy-3,6-di(4',5'-dicyanoimidazol-2'-ylaminocarbonyl)naphthalene (3.5 g) was obtained as a skin colored powder (melting point: 256.8° C.) by the same procedure as that described in Example 2 with the exception of using 2-amino-4,5-dicyanoimidazole (8.3 g) instead of 2-aminothiazole.

Figure 4:
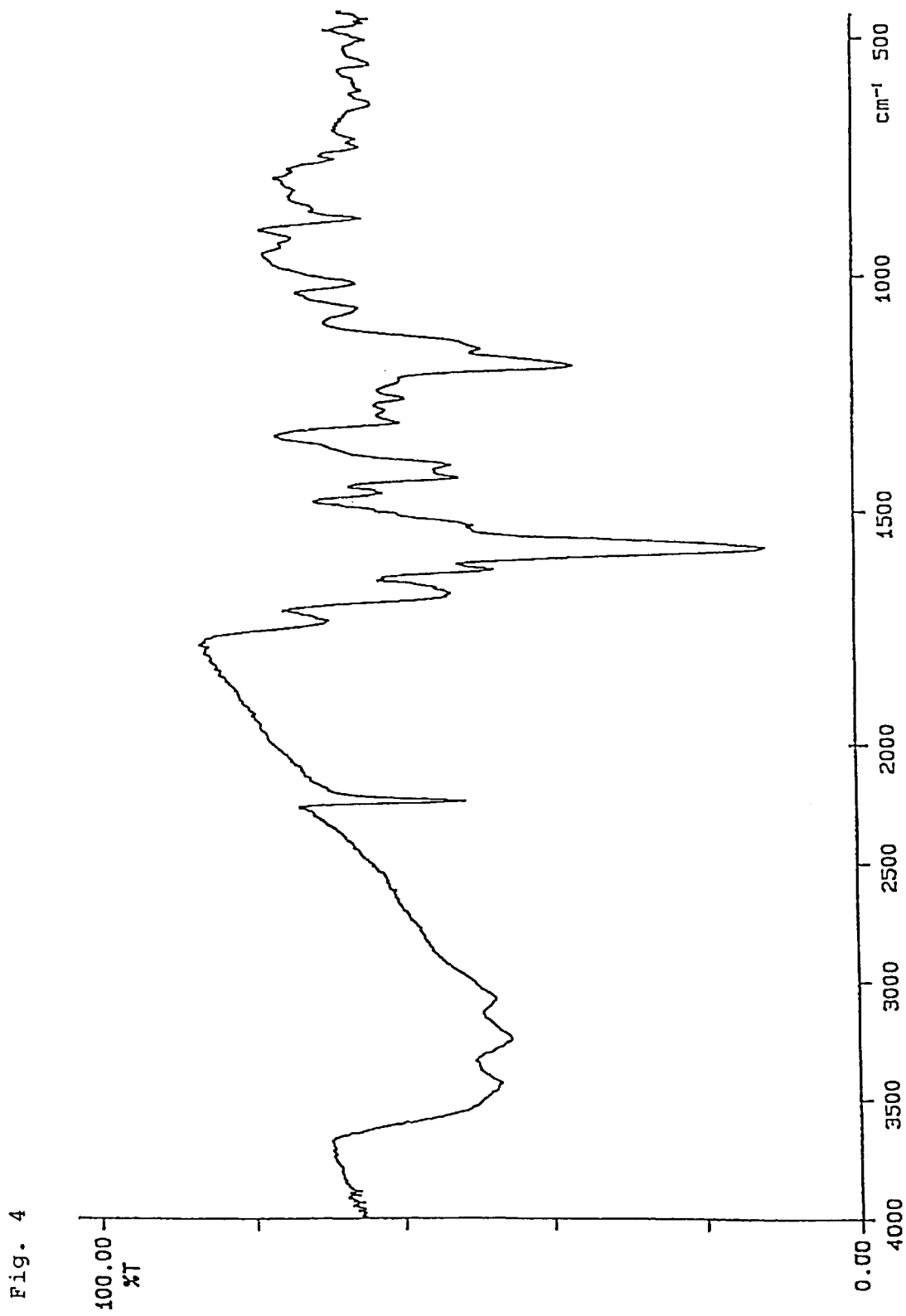
FIG. 4 is an infrared absorption spectrum of the compound obtained in Example 4.

An infrared absorption spectrum (KBr method) is shown in FIG. 4.

Example 5

Synthesis of 2-hydroxy-3-methoxycarbonyl-6-(benzothiazol-2'-ylaminocarbonyl)naphthalene

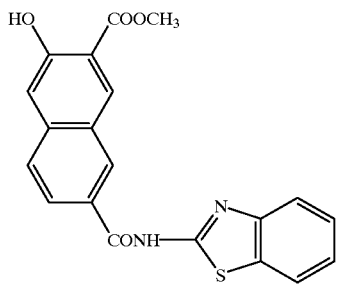

2-Hydroxy-3-methoxycarbonyl-6-(benzothiazol-2'-ylaminocarbonyl)naphthalene (3.5 g) was obtained as a pale yellow powder (decomposition point: 375.3° C.) by the same procedure as that described in Example 3 with the exception of using 2-hydroxy-3-methoxycarbonyl-6-chlorocarbonylnaphthalene (2.6 g) instead of 2-hydroxy-3,6-bischlorocarbonylnaphthalene.

Figure 5:
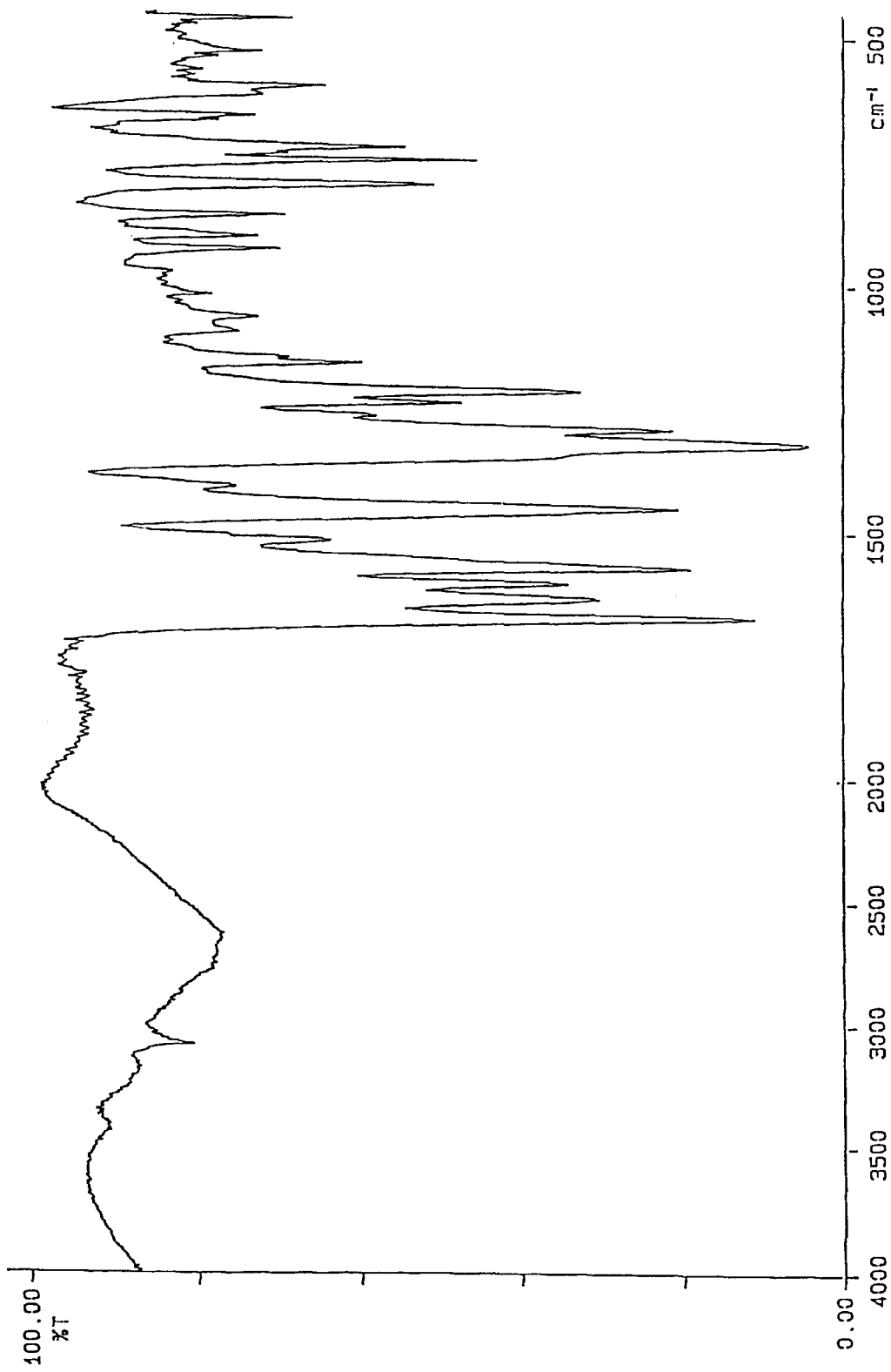
FIG. 5 is an infrared absorption spectrum of the compound obtained in Example 5.

An infrared absorption spectrum (KBr method) is shown in FIG. 5.

Example 6

Synthesis of 2-hydroxy-6-methoxycarbonyl-3-(4',5'-dicyanoimidazol-2'-ylaminocarbonyl)naphthalene

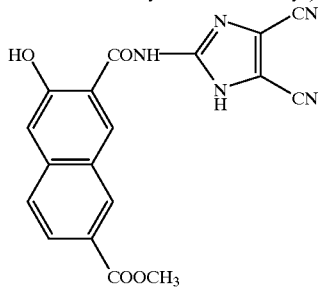

2-Hydroxy-6-methoxycarbonyl-3-(4',5'-dicyanoimidazol-2'-ylaminocarbonyl)naphthalene (5.0 g) was obtained as a pale brown powder (decomposition point: 323.1° C.) by the same procedure as that described in Example 3 with the exception of using 2-hydroxy-6-methoxycarbonyl-3-chlorocarbonylnaphthalene (5.3 g) instead of 2-hydroxy-3,6-bischlorocarbonylnaphthalene.

Figure 6:
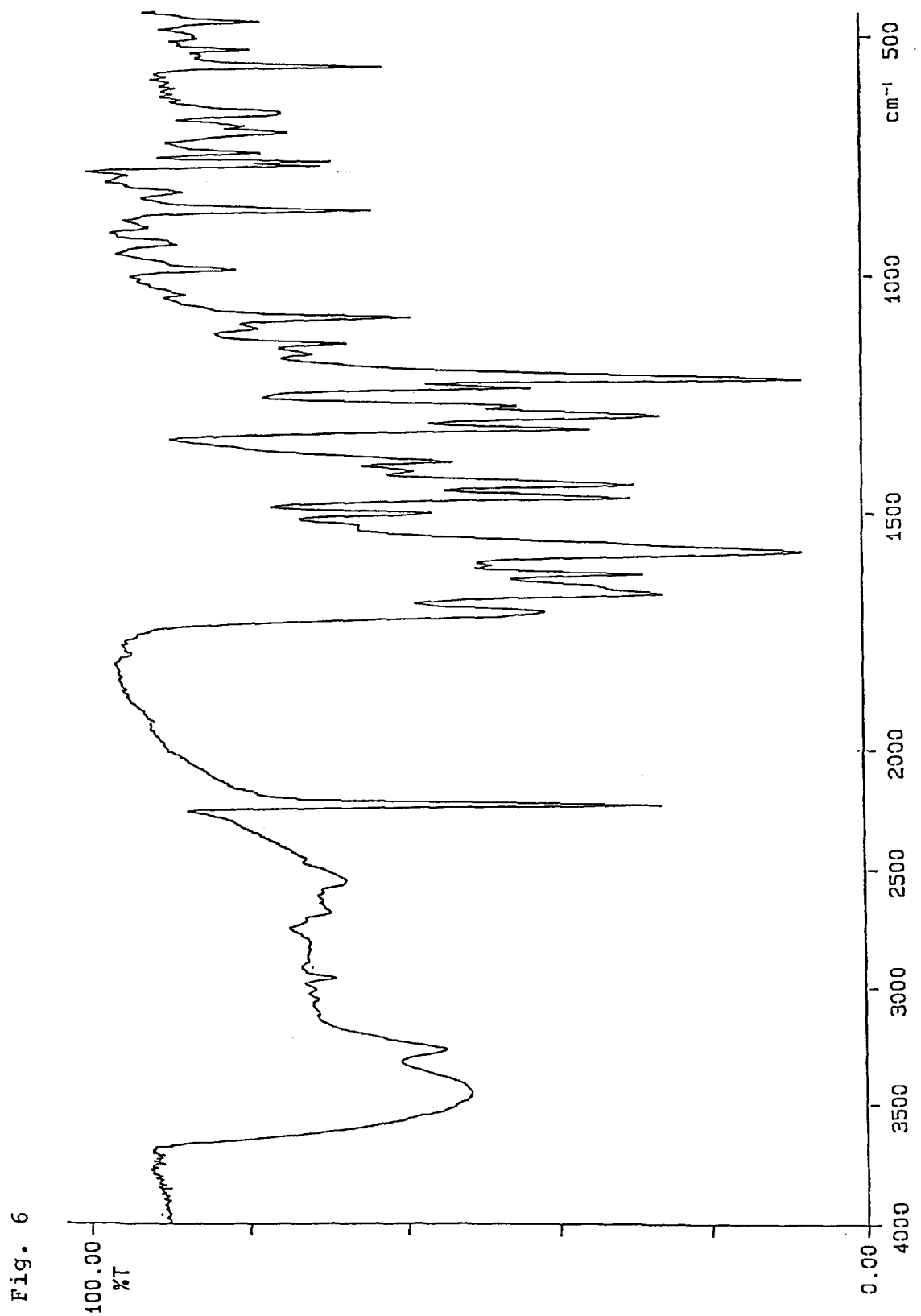
FIG. 6 is an infrared absorption spectrum of the compound obtained in Example 6.

An infrared absorption spectrum (KBr method) is shown in FIG. 6.

What is claimed is:

1. A naphthol compound represented by the formula (I):

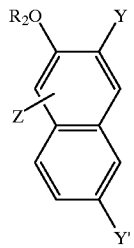

(I)

wherein Y is —(CONH)$_n$—X or —COR, and

Y' is —(CONH)$_n$—X' or —COR';

X and X' may be the same or different and represent a pyridyl group, a thiazolyl group, a benzothiazolyl group or an imidazolyl group, and each group may be optionally substituted;

R and R' may be the same or different and represent a hydroxyl group, an optionally branched alkoxy group having 1 to 6 carbon atoms, a halogen atom, a benzyloxy group, a phenyloxy group or a phenacyloxy group;

$R_2$ is a hydrogen atom, an alkali metal, an optionally branched alkyl group having 1 to 6 carbon atoms, an acyl group having 1 to 6 carbon atoms or a phenylalkylene group, Z, which may be substituted on any ring of the naphthalene ring, is at least one moiety selected from the group consisting of a hydrogen atom, a halogen atom, a nitro group, a nitroso group and an amino group, and n is an integer of 1 or 2; provided that Y and Y' are not simultaneously —COR and —COR', respectively.

2. The naphthol compound according to claim 1, wherein Y' is —(CONH)$_n$—X and the other is —(CONH)$_n$—X'.

3. A process for producing the naphthol compound of claim 2, which comprises condensing a naphthol compound represented by the formula (II):

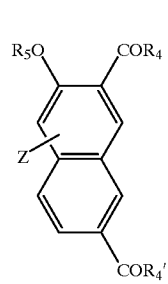

(II)

wherein one of the substituents $R_4$ and $R_4'$ is a hydroxyl group or a halogen atom and the other is a hydroxyl group, a halogen atom, an optionally branched alkoxy group having 1 to 6 carbon atoms, a benzyloxy group, a phenyloxy group or a phenacyloxy group; $R_5$ is a hydrogen atom or a protective group of a hydroxyl group;

with a heterocyclic compound represented by the formula (III):

$H_2N$—$R_3$—X (III)

wherein $R_3$ is a single bond or —CONH—.

* * * * *